(12) United States Patent
Kang et al.

(10) Patent No.: US 10,426,436 B2
(45) Date of Patent: Oct. 1, 2019

(54) ULTRASONIC IMAGING APPARATUS AND CONTROL METHOD THEREOF

(71) Applicant: SAMSUNG ELECTRONICS CO., LTD., Suwon-si (KR)

(72) Inventors: Joo Young Kang, Yongin-si (KR); Sung Chan Park, Suwon-si (KR); Kyu Hong Kim, Seongnam-si (KR); Jung Ho Kim, Yongin-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 467 days.

(21) Appl. No.: 14/270,920

(22) Filed: May 6, 2014

(65) Prior Publication Data

US 2014/0330126 A1 Nov. 6, 2014

(30) Foreign Application Priority Data

May 6, 2013 (KR) .................. 10-2013-0050928

(51) Int. Cl.
*B06B 1/06* (2006.01)
*A61B 8/00* (2006.01)
*A61B 8/08* (2006.01)
*A61B 8/14* (2006.01)
(Continued)

(52) U.S. Cl.
CPC ............ *A61B 8/4494* (2013.01); *A61B 8/145* (2013.01); *A61B 8/4488* (2013.01); *A61B 8/463* (2013.01); *A61B 8/5207* (2013.01); *A61B 8/54* (2013.01); *G01S 15/895* (2013.01); *G01S 15/8915* (2013.01); *G01S 15/8929* (2013.01); *G10K 11/34* (2013.01); *A61B 8/14* (2013.01); *A61B 8/46* (2013.01); *A61B 8/483* (2013.01);
(Continued)

(58) Field of Classification Search
CPC .......... A61B 8/483; A61B 8/14; A61B 8/463; B06B 1/0629; G10K 11/346
See application file for complete search history.

(56) References Cited

U.S. PATENT DOCUMENTS 4,307,613 A * 12/1981 Fox ...................... G01N 29/262
367/105
6,063,030 A * 5/2000 Vara ...................... G16H 40/63
600/437
(Continued)

FOREIGN PATENT DOCUMENTS

JP 4897370 B2 3/2012
KR 10-0793382 B1 1/2008
(Continued)

*Primary Examiner* — Jonathan Cwern
(74) *Attorney, Agent, or Firm* — Sughrue Mion, PLLC

(57) ABSTRACT

An ultrasonic probe includes a multi-dimensionally arrayed transducer, a matching layer, and a backing layer. The transducer includes element groups having different focal distances and simultaneously transmitting ultrasonic signals toward an object. According to the ultrasonic imaging apparatus using the multi-dimensionally arrayed transducer, a multi-focus transmission is performed. Thus, the multi-focus ultrasonic image may be acquired within a short period of time, thereby increasing frame rates, and a high-quality image in which all areas are focused may be quickly acquired.

15 Claims, 20 Drawing Sheets

(51) Int. Cl.
*G01S 15/89* (2006.01)
*G10K 11/34* (2006.01)

(52) U.S. Cl.
CPC .............. *A61B 8/543* (2013.01); *A61B 8/56* (2013.01); *B06B 1/0629* (2013.01); *G10K 11/346* (2013.01)

(56) References Cited

U.S. PATENT DOCUMENTS

| | | | |
|---|---|---|---|
| 6,104,670 A * | 8/2000 | Hossack | G01N 29/2456 367/11 |
| 2001/0020131 A1* | 9/2001 | Kawagishi | G01S 7/52046 600/443 |
| 2002/0139193 A1 | 10/2002 | Angelsen et al. | |
| 2002/0145941 A1 | 10/2002 | Poland et al. | |
| 2003/0018261 A1 | 1/2003 | Bae | |
| 2005/0148877 A1* | 7/2005 | Guo | A61B 8/14 600/459 |
| 2010/0049053 A1* | 2/2010 | Yamamoto | G01S 7/52084 600/459 |
| 2011/0066032 A1* | 3/2011 | Vitek | A61N 7/02 600/459 |
| 2011/0094288 A1* | 4/2011 | Medan | G10K 11/346 73/1.82 |
| 2013/0253325 A1* | 9/2013 | Call | G01S 15/8952 600/447 |

FOREIGN PATENT DOCUMENTS

| KR | 10-2011-0003057 A | 1/2011 |
|---|---|---|
| KR | 10-2012-0030488 A | 3/2012 |

* cited by examiner

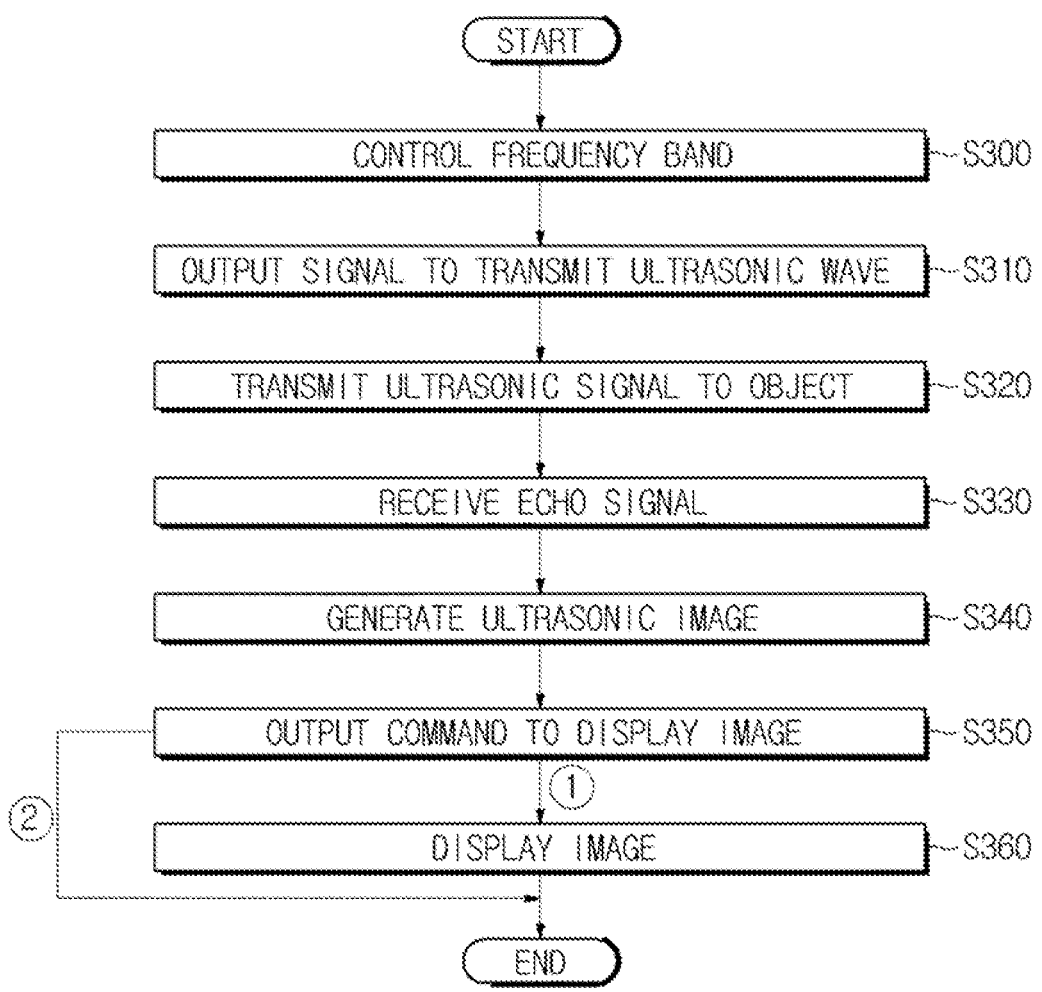

ULTRASONIC IMAGING APPARATUS AND CONTROL METHOD THEREOF

CROSS-REFERENCE TO RELATED APPLICATION

This application claims priority from Korean Patent Application No. 10-2013-0050928, filed on May 6, 2013 in the Korean Intellectual Property Office, the disclosure of which is incorporated herein by reference in its entirety.

BACKGROUND

1. Field

Apparatuses and methods consistent with exemplary embodiments relate to an ultrasonic imaging apparatus using multi-dimensionally arrayed transducers and a method of controlling the same.

2. Description of the Related Art

An ultrasonic imaging apparatus transmits ultrasonic waves toward a target region of an object from the surface of the object and detects reflected signals from the target region, i.e., ultrasonic echo signals, to generate an image of the target region, thereby providing information regarding the target region.

The ultrasonic imaging apparatus is small and inexpensive, as compared to other imaging apparatuses, and is thus widely used for diagnostic purposes due to non-invasive and nondestructive characteristics.

The ultrasonic imaging apparatus includes an ultrasonic probe to transmit ultrasonic waves to a target region of an object and to receive echo signals reflected from the object in order to acquire an ultrasonic image. The ultrasonic probe includes a transducer that converts an electrical signal into a sound wave and vice versa.

SUMMARY

One or more of exemplary embodiments provide an ultrasonic imaging apparatus using a multi-dimensionally arrayed transducer that performs multi-focal transmission and a method of controlling the ultrasonic imaging apparatus.

In accordance with an aspect of an exemplary embodiment, an ultrasonic probe, which transmits ultrasonic signals toward an object and receives echo signals reflected from the object, includes a multi-dimensionally arrayed transducer to convert an electrical signal into an ultrasonic signal and vice versa, a matching layer to reduce an acoustic impedance difference between the transducer and an object, and a backing layer to block ultrasonic waves generated by the transducer from proceeding in the backward direction of the transducer. The transducer includes a plurality of element groups having different focal distances, and the plurality of element groups simultaneously transmits ultrasonic signals toward the object The ultrasonic probe include a multi-dimensionally arrayed transducer including plurality of element groups, which simultaneously transmit ultrasonic signals having different frequencies toward the object according to the focal distance.

The ultrasonic probe may further include a controller to control a frequency band of the transmitted ultrasonic signal.

In accordance with another aspect of an exemplary embodiment, an ultrasonic imaging apparatus includes an ultrasonic probe including a multi-dimensionally arrayed transducer to transmit ultrasonic signals toward an object and receive echo signals reflected from the object, a controller to output a control command signal to cause the ultrasonic probe to transmit the ultrasonic signals, and an image processor to generate an image corresponding to the echo signals. The transducer includes a plurality of element groups having different focal distances and the plurality of element groups simultaneously transmits ultrasonic signals toward the object The ultrasonic imaging apparatus may further include a display that displays an image generated by the image processor.

The ultrasonic imaging apparatus may include an ultrasonic probe including a multi-dimensionally arranged transducer including a plurality of element groups that simultaneously transmit ultrasonic signals having different frequencies according to focal distance.

The ultrasonic imaging apparatus may further include a controller to control a frequency band of ultrasonic signal.

In accordance with another aspect of an exemplary embodiment, a method of controlling an ultrasonic probe includes simultaneously transmitting ultrasonic signals toward an object by a plurality of element groups having different focal distances and receiving a plurality of echo signals from the object by the plurality of element groups The simultaneously transmitting of the ultrasonic signals may be performed by simultaneously transmitting ultrasonic signals having different frequencies toward the object according to the focal distance.

The method may further include controlling a frequency band of the transmitted ultrasonic signal.

In accordance with an aspect of an exemplary embodiment, a method of controlling an ultrasonic imaging apparatus includes simultaneously transmitting ultrasonic signals toward an object by a plurality of element groups having different focal distances, receiving a plurality of echo signals from the object by the plurality of element groups, and generating an image corresponding to the plurality of echo signals.

The simultaneously transmitting of the ultrasonic signals is performed by simultaneously transmitting ultrasonic signals having different frequencies toward the object according to the focal distance.

The method may further include controlling a frequency band of the transmitted ultrasonic signal.

BRIEF DESCRIPTION OF THE DRAWINGS

The and/or other aspects will become more apparent by describing certain exemplary embodiments, with reference to the accompanying drawings, in which:

FIG. 13 is a flowchart illustrating a method of controlling an ultrasonic imaging apparatus according to an exemplary embodiment.

DETAILED DESCRIPTION

Figure 1:
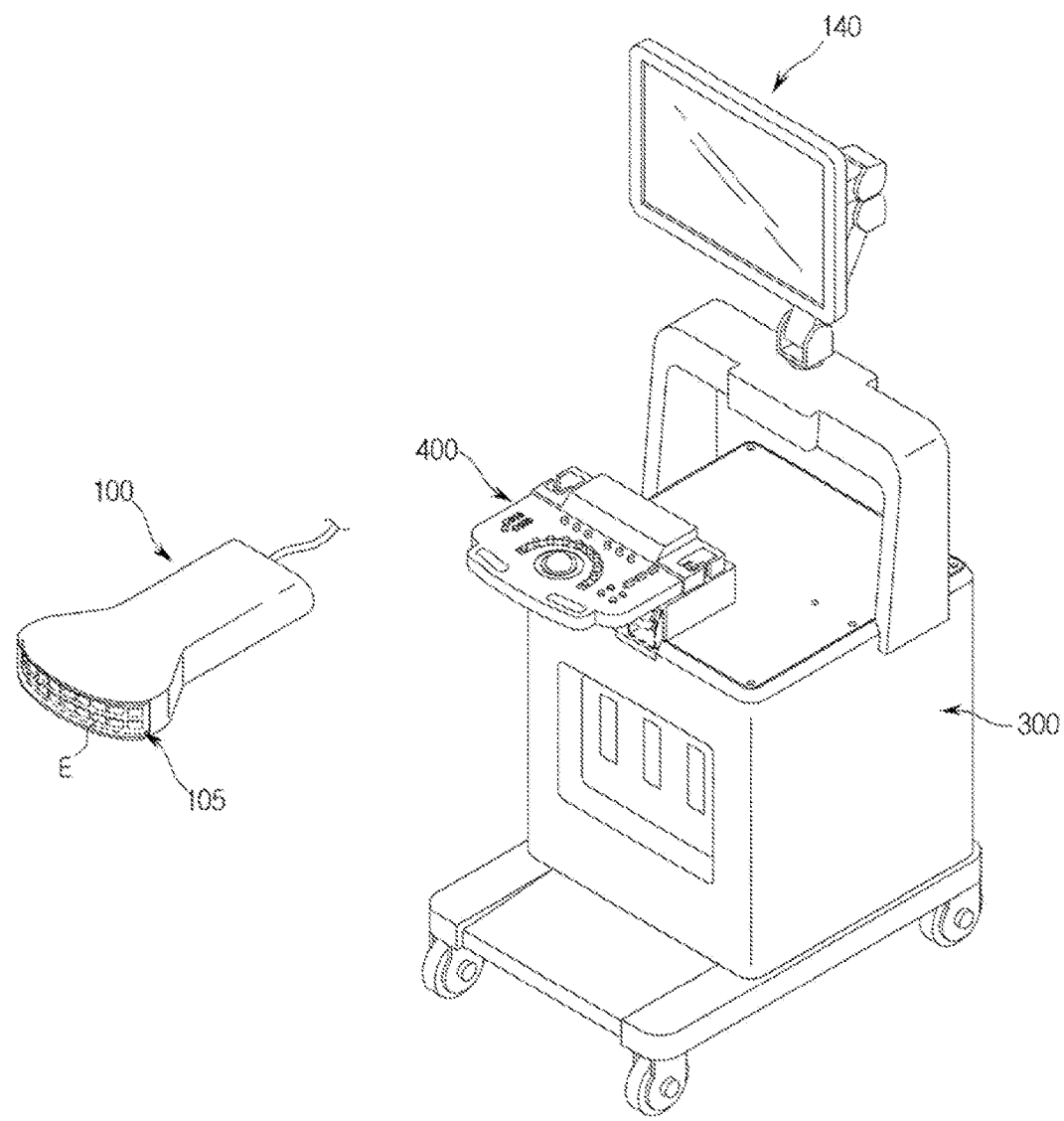
FIG. 1 is a perspective view illustrating an ultrasonic imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a perspective view illustrating an ultrasonic imaging apparatus according to an exemplary embodiment.

As illustrated in FIG. 1, an ultrasonic imaging apparatus includes a probe 100, a main body 300, an input unit 400, and a display 140.

The probe 100 is connected to one end of a cable, and a male connector (not shown) is connected to the other end of the cable. The male connector may be physically coupled to a female connector (not shown) of the main body 300.

The probe 100 may transmit ultrasonic signals toward an object and receive echo signals, i.e., ultrasonic signals, reflected from the object to acquire an ultrasonic image of a target region of the object to be diagnosed. The object may be a living body, a blood vessel, a bone, a muscle, and the like, of human or animals, but is not limited thereto.

The probe 100 may directly contact the object or transmit and receive ultrasonic signals outside the object in a non-contact state. For example, during ultrasonic imaging of a fetus (target region), the probe 100 directly contacts the abdomen (object) of a mother. However, during ultrasonic imaging of a tumor (target region) of a liver, the probe 100 does not directly contact the liver of a patient (object) but contacts the abdomen of the patient.

Figure 10:
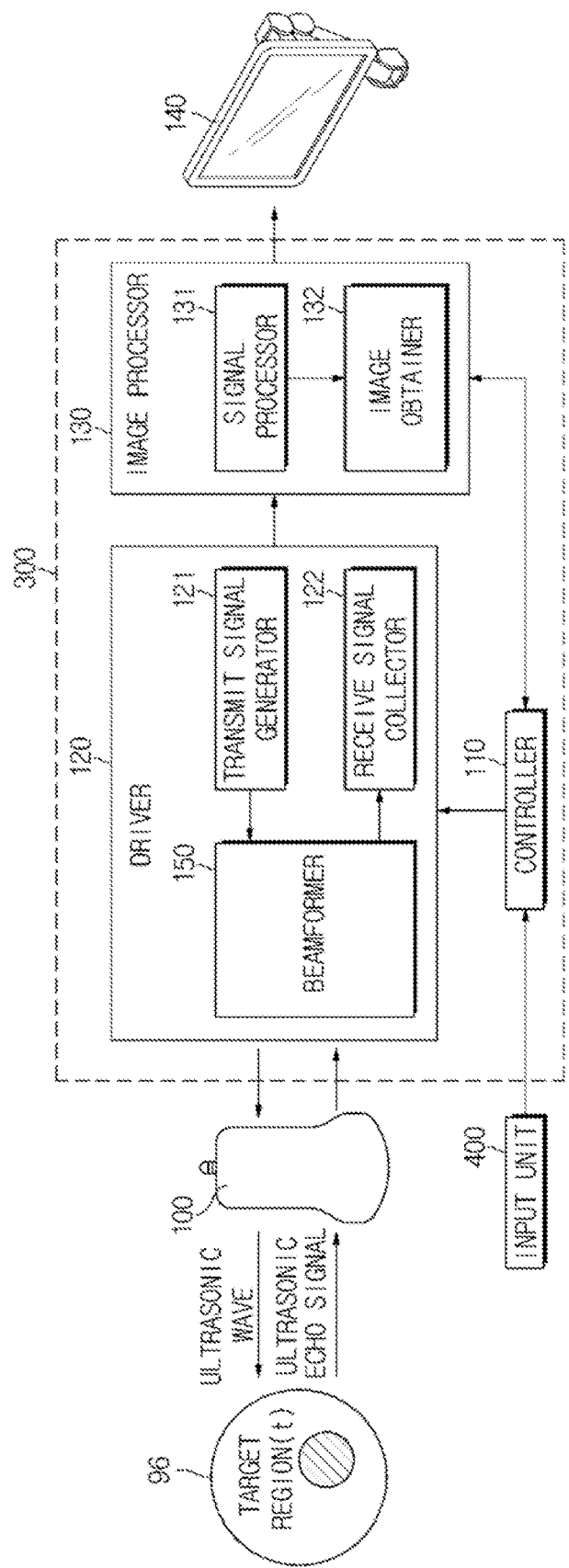
FIG. 10 is a block diagram illustrating an ultrasonic imaging apparatus according to an exemplary embodiment.

The main body 300 may accommodate major constituent elements of the ultrasonic imaging apparatus, for example, a driver 120 (FIG. 10). When a user inputs a command to initiate ultrasonic imaging, the driver 120 may generate a driving signal and transmit the driving signal to the probe 100.

The main body 300 may have at least one female connector (not shown). The female connector may be physically connected to the male connector (not shown) connected to the cable such that the main body 300 and the probe 100 may transmit and receive signals respectively generated thereby. For example, the driving signal generated by the driver 120 may be transmitted to the probe 100 through the male connector connected to the female connector of the main body 300 and the cable.

In addition, a plurality of casters capable of fixing the ultrasonic imaging apparatus to a predetermined position or moving the ultrasonic imaging apparatus in a predetermined direction may be installed at lower portions of the main body 300.

The input unit 400 receives an input command regarding operation of the ultrasonic imaging apparatus. For example, the input unit 400 may receive a command to initiate ultrasonic imaging or a frequency band of the ultrasonic signal transmitted from the probe 100. The command input by the input unit 400 may be transmitted to the main body 300 via a wired or wireless communication network.

The input unit 400 may include at least one of a switch, a keyboard, a trackball, and a touchscreen, but is not limited thereto.

The input unit 400 may be disposed at an upper portion of the main body 300 as illustrated in FIG. 1. However, a foot switch, a foot pedal, and the like may also be disposed at lower portions of the main body 300.

At least one probe holder to hold the probe 100 may be mounted around the input unit 400. Thus, the user may store the probe in the probe holder when the ultrasonic imaging apparatus is not in use.

The display 140 may display an ultrasonic image acquired during the ultrasonic imaging on a screen. The display 140 may be coupled to the main body 300, or may be implemented detachably from the main body 300.

Although not illustrated in FIG. 1, the display 140 may include a separate sub-display that displays applications regarding operation of the ultrasonic imaging apparatus, such as a menu or guidelines for ultrasonic examination.

The display 140 may be a cathode ray tube (CRT) or a liquid crystal display (LCD), but is not limited thereto.

Hereinafter, the probe 100 will be described in more detail with reference to FIGS. 2 to 9.

Figure 2:
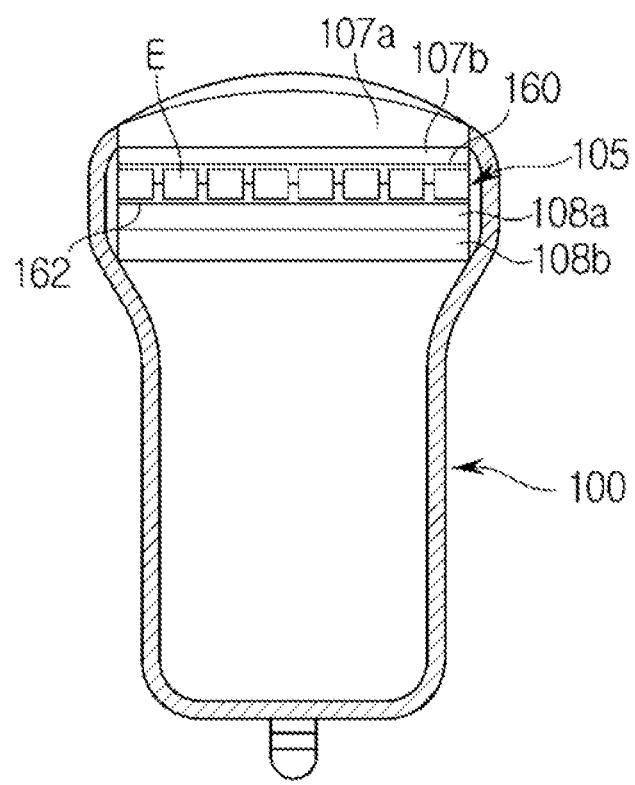
FIG. 2 is a cross-sectional view illustrating an ultrasonic probe according to an exemplary embodiment.

FIG. 2 is a cross-sectional view illustrating an ultrasonic probe according to an exemplary embodiment.

Referring to FIG. 2, the probe 100 includes a transducer 105 including a plurality of elements E, matching layers 107a and 107b disposed on the front surface 160 of the transducer 105, and backing layers 108a and 108b disposed on the rear surface 162 of the transducer 105.

The transducer 105 serves to perform interconversion between an electrical signal and an ultrasonic signal. When the probe 100 receives current from an external power supply device or an internal power storage device such as a battery, the elements E of the transducer 105 vibrate to generate ultrasonic waves. The generated ultrasonic waves are radiated to an external object. The ultrasonic waves are reflected from the object, and the elements E receive the reflected ultrasonic echo signals. The elements E vibrate in response to the received ultrasonic echo signals, thereby generating current having frequencies corresponding to the vibration frequencies thereof.

The matching layers 107a and 107b reduce an acoustic impedance difference between the transducer 105 and the object so as to maximally transmit ultrasonic waves generated by the transducer 105 to the object or ultrasonic echo signals reflected from the object to the transducer 105. When a plurality of matching layers 107a and 107b is used as illustrated in FIG. 2, the acoustic impedance difference may be reduced in a stepwise manner.

The backing layers 108a and 108b are formed of materials capable of absorbing ultrasonic waves so as to block the ultrasonic waves from proceeding in the backward direction of the transducer 105, which may inhibit image distortion. The backing layer may include a plurality of layers to improve ultrasonic wave blocking efficiency.

Figure 3A:
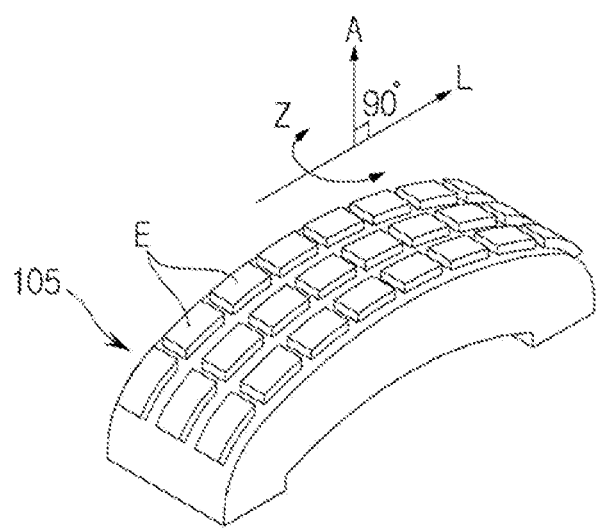
FIGS. 3A, 3B, and 3C illustrate views of multi-dimensionally arrayed transducers.
Figure 3B:
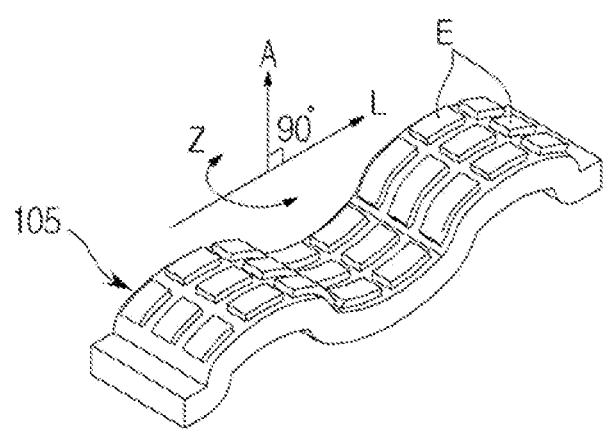
Figure 3C:
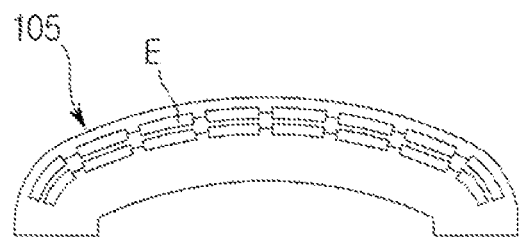
Figure 4:
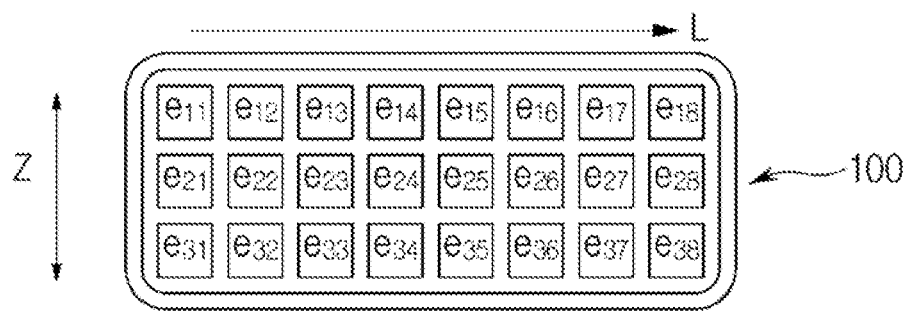
FIG. 4 is a front view illustrating a probe including a multi-dimensionally arrayed transducer according to an exemplary embodiment.

FIGS. 3A to 3C illustrate views of multi-dimensionally arrayed transducers. FIG. 4 is a front view illustrating a probe including a multi-dimensionally arrayed transducer according to an exemplary embodiment.

The transducer 105 that is a more than two-dimensional transducer, i.e., a multi-dimensionally arrayed transducer, may be constructed in various forms in accordance with the array of the plurality of elements E.

For example, as illustrated in FIG. 3, a proceeding direction of ultrasonic waves is referred to as an axial direction A, a direction perpendicular to the proceeding direction of ultrasonic waves is referred to as a lateral direction L, and a left-right direction based on the plane defined by the axial direction A and the lateral direction L is referred to as an azimuth direction Z. The elements E may be arrayed to protrude in the axial direction A, so that the transducer 105 may have an overall convex shape (FIG. 3A). The transducer 105 may have a waveform in which the elements E having concave and convex shapes, with respect to the axial direction A, are combined (FIG. 3B).

Furthermore, as illustrated in FIG. 3C, the elements E illustrated in FIG. 3A may be stacked in the axial direction A.

As described above, the transducer 105 may be constructed in various forms. However, the elements E have a two-dimensional array, when viewed from the front side thereof. Thus, when the transducer 105 of the probe 100 includes m elements E disposed in the lateral direction L and n elements E disposed in the azimuth direction Z, when viewed from the front view of the probe 100, m≥2, and n≥2.

For example, the elements E (e11, e12, . . . , e18, e21, e22, . . . , e28, e31, e32, . . . , e38) may be arrayed such that eight elements E are disposed in the lateral direction L and three elements E are disposed in the azimuth direction Z as illustrated in FIG. 4.

Figure 5:
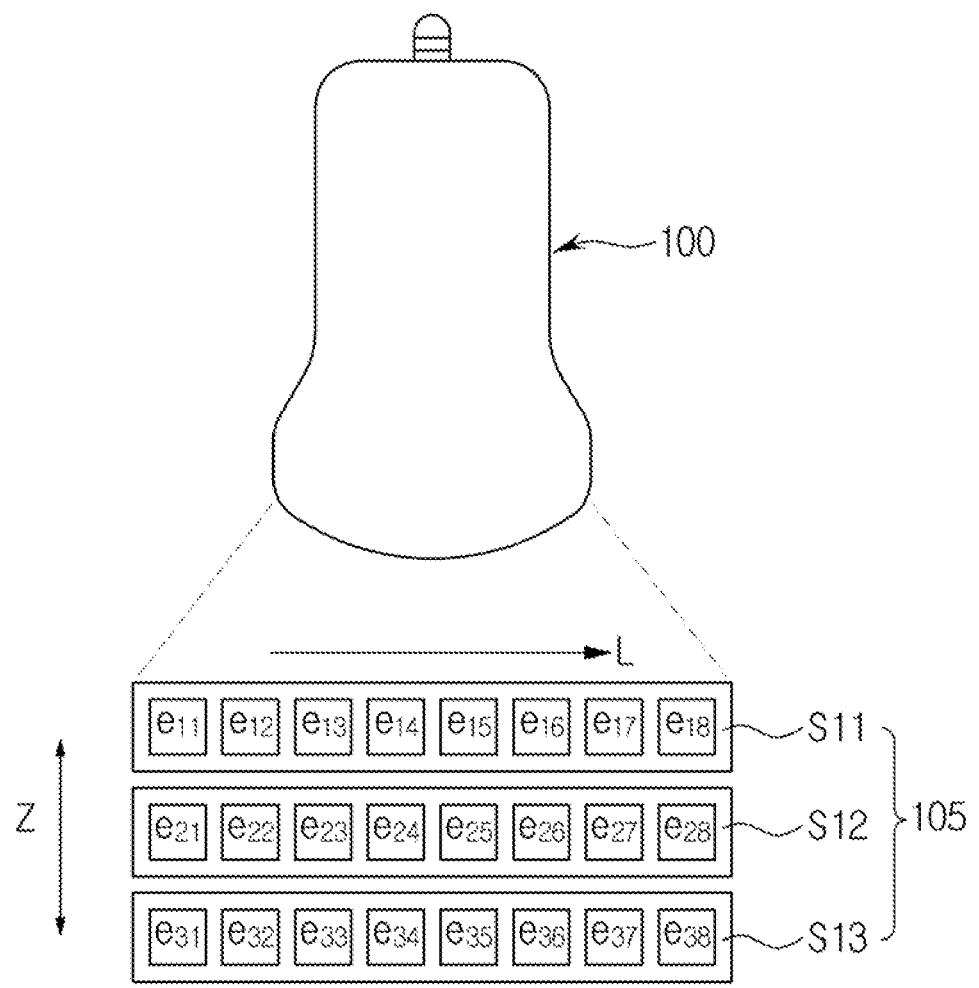
FIG. 5 is a diagram illustrating groups of elements respectively disposed in a transducer.

FIG. 5 is a diagram illustrating groups of the plurality of elements respectively disposed in transducers.

The aforementioned transducer 105 has a plurality of focus points according to the target region of the object or the type of element. Thus, elements used to transmit ultrasonic signals onto the predetermined focus point need to be classified into a plurality of groups corresponding to the number of focus points.

FIG. 5 illustrates the elements E of FIG. 4 rotated by 90° with respect to the lateral direction L and viewed from the front side of the probe 100 in order to describe a method of grouping the elements E, and the aforementioned array and directions of the array are not substantially changed. As illustrated in FIG. 5, for example, the elements E may be grouped in the lateral direction L. That is, the elements e11, e12, . . . , and e18 may be defined as a first group s11, the elements e21, e22, . . . , and e28 may be defined as a second group s12, and the elements e31, e32, . . . , and e38 may be defined as a third group s13.

As another example, the elements E may be grouped in the azimuth direction Z. That is, referring to FIG. 5, the elements e11, e21, and e31 may be defined as a first group, the elements e12, e22, and e32 may be defined as a second group, . . . , and the elements e18, e28, and e38 may be defined as an eighth group, i.e., the elements E may be classified into eight groups.

However, the grouping of the elements according to an exemplary embodiment is limited to the above and the elements may be grouped in a different manner.

The elements E classified as described above are referred to as a plurality of element groups s11, s12, and s13 in FIG. 5. A method of transmitting ultrasonic signals by the probe 100 via the plurality of element groups will be described.

Figure 6A:
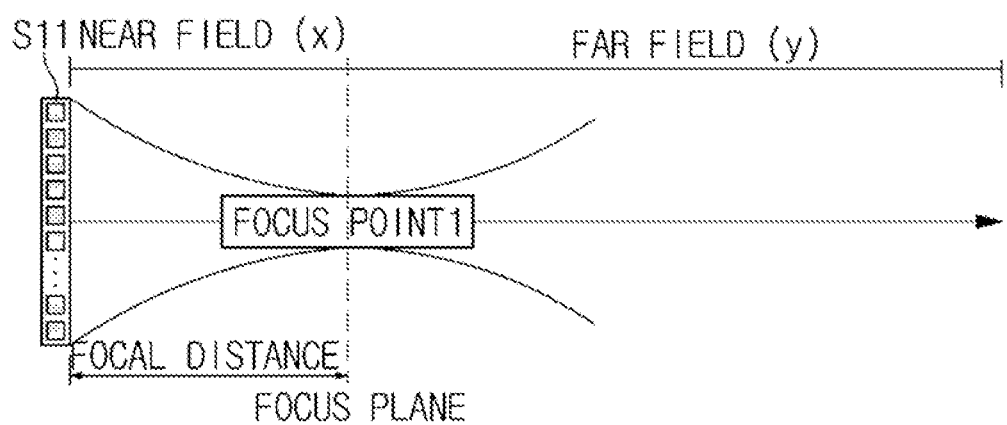
FIGS. 6A, 6B, and 6C are diagrams for describing a method of transmitting ultrasonic signals through multiple focus points according to an exemplary embodiment.
Figure 6B:
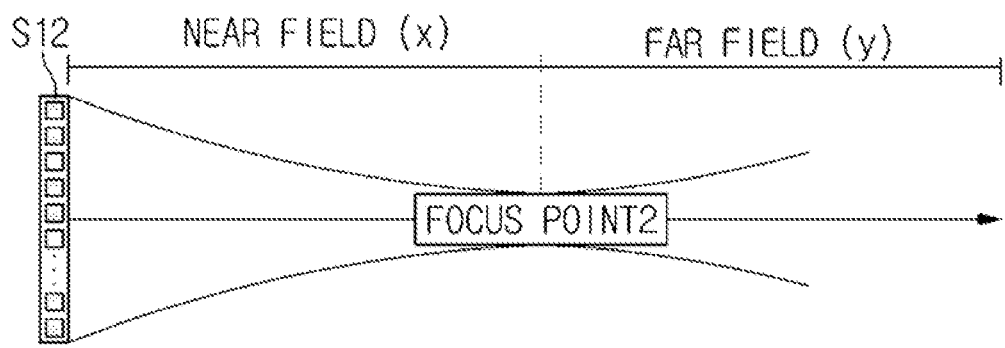
Figure 6C:
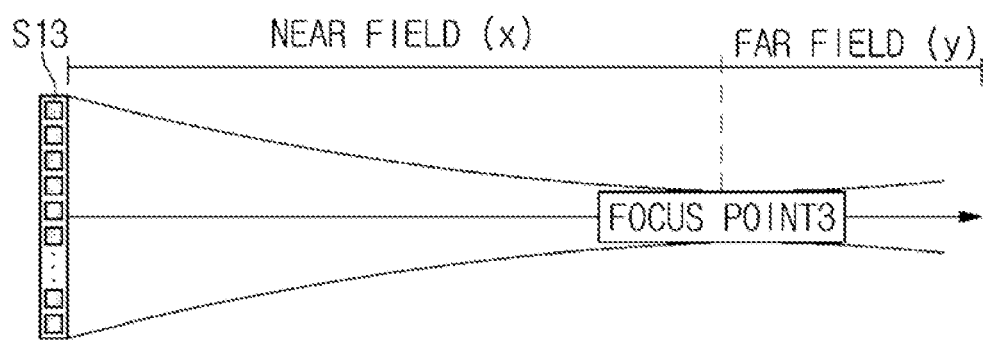
Figure 7A:
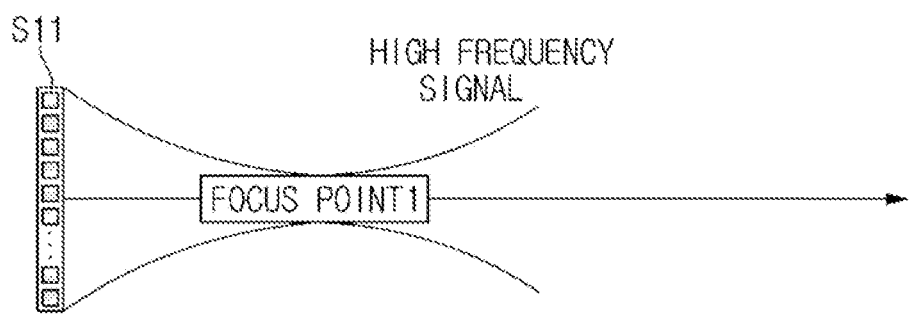
FIGS. 7A, 7B, and 7C are diagrams for describing a method of transmitting ultrasonic signals having different frequencies according to focal distance according to an exemplary embodiment.
Figure 7B:
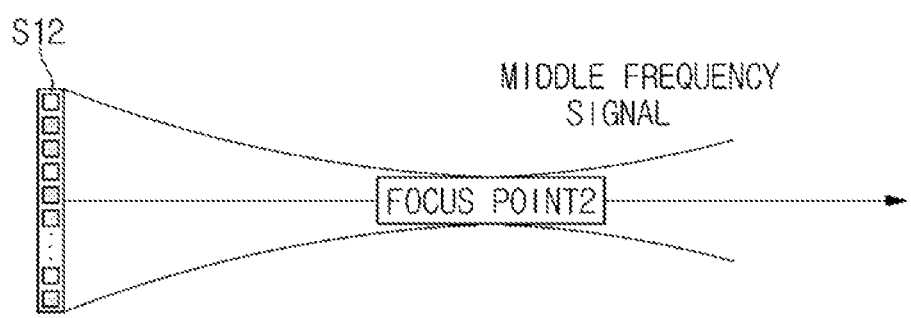
Figure 7C:
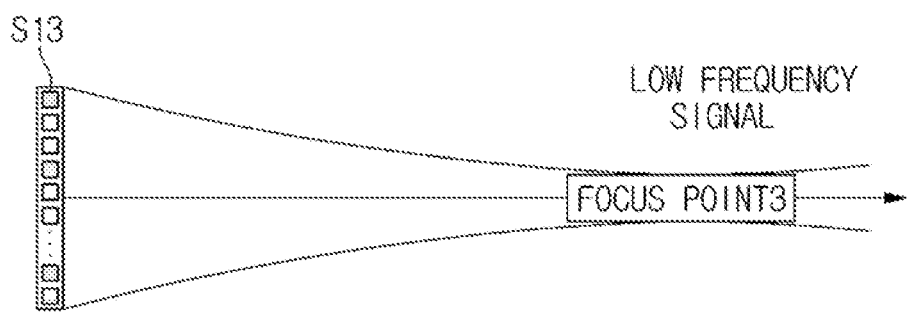

FIGS. 6A to 6C are diagrams for describing a method of transmitting ultrasonic signals through multiple focus points according to an exemplary embodiment. FIGS. 7A to 7C are diagrams for describing a method of transmitting ultrasonic signals having different frequencies according to focal distance according to an exemplary embodiment.

Before the element groups transmit ultrasonic signals, focus points need to be set. The focus points may be set such that the element groups have different focal distances while considering significance of resolution.

For example, focus points are set such that focal distances of the element groups are different. That is, since the element groups have different focal distances, no two element groups have the same focal distance. Here, the focal distance is a vertical distance from the center of each of the element groups to a respective focus plane.

As illustrated in FIG. 5, for example, the element groups may have different focal distances such that the first group s11 has a near field focus point, the second group s12 has a middle field focus point, and the third group s13 has a far field focus point.

The near field focus point of the first group s11 is referred to as Focus Point 1, the middle field focus point of the second group s12 is referred to as Focus Point 2, and the far field focus point of the third group s13 is referred to as Focus Point 3. Thus, the element groups may have different focal distances, and the elements E belonging to each group have the same focal distance.

For example, the significance of the resolution is considered while setting the focus points.

Referring to FIG. 6A, ultrasonic waves generated by the elements E proceed in the axial direction A by a predetermined distance, and then radiate thereafter. When a region before the ultrasonic waves radiate is referred to as a near field x, and a region after the ultrasonic waves radiate is referred to as a far field y, the resolution of an ultrasonic image of the near field x is significant.

Particularly, since a high resolution may be obtained at an end portion of the near field x, the focus points of the element groups are set such that the target region of the object is located at end portions of the near field x.

Based on the preset focus points, the element groups having different focal distances may simultaneously transmit ultrasonic signals toward the object.

Referring to FIGS. 6A to 6C, the element groups s11, s12, and s13 having different focal distances, i.e., the first group s11 having a near field focus point referred to as Focus Point 1, the second group s12 having a middle field focus point referred to as Focus Point 2, and the third group s13 having a far field focus point referred to as Focus Point 3 may simultaneously transmit ultrasonic waves toward the object.

The element groups having different focal distances may simultaneously transmit ultrasonic signal having different frequencies in accordance with the respective focal distances to the object. In this regard, the focal distance and the transmit frequency corresponding to the focal distance are inversely proportional to each other.

For example, as illustrated in FIGS. 7A to 7C, the first group s11 having the near field focus point (Focus Point 1) may transmit a high frequency signal, the second group s12 having the middle field focus point (Focus Point 2) may transmit a middle frequency signal, and the third group s13 having the far field focus point (Focus Point 3) may transmit a low frequency signal. The first group s11, the second group s12, and the third group s13 may simultaneously transmit the ultrasonic signals.

Changing of the frequency according to the focal distance as described above is related to attenuation and resolution, which will be described below.

Ultrasonic waves that are sound waves are reflected, scattered, and absorbed, and the like, and accordingly, attenuation by which intensity of an ultrasonic signal gradually decreases occurs as a distance to the target region of the object increases. As frequency increases, the degree of attenuation increases. Thus, ultrasonic waves having a high frequency cannot reach the far field.

Meanwhile, resolution of ultrasonic waves capable of distinguish two different objects in an image display device may be classified into axial resolution that is an ability to distinguish two objects arrayed in the ultrasonic wave proceeding direction and lateral resolution that is an ability to distinguish two objects aligned in a direction perpendicular to the ultrasonic wave proceeding direction.

Thus, a high frequency ultrasonic signal that improves resolution is transmitted in the near field focus point region since the degree of attenuation thereof is negligible in comparison to the focal distance. A low frequency ultrasonic signal that undergoes less attenuation is transmitted in the far field focus point to allow the ultrasonic waves to reach the far field although the resolution may decrease. As a result, a high-quality multi-focus ultrasonic image may be acquired.

Thus, referring to FIGS. 7A to 7C, ultrasonic signals having different frequencies may be transmitted.

The first group s11 having the near field focus point (Focus Point 1) transmits higher frequency ultrasonic signals capable of improving resolution toward the object, and the third group s13 having the far field focus point (Focus Point 3) transmits ultrasonic signals having a lower degree of attenuation toward the object. Thus, the plurality of element groups having different focal distances may transmit ultrasonic signals with different frequencies in inverse proportion to the focal distances.

The method of transmitting ultrasonic waves by the probe 100 according to exemplary embodiments has been described.

The transducer 105 of the probe 100 may be a magnetostrictive ultrasonic transducer using magnetostrictive effects of a magnetic substance, a capacitive micromachined ultrasonic transducer (cMUT), which transmits and receives ultrasonic waves using vibration of several hundreds or several thousands of micromachined thin films, or a piezoelectric ultrasonic transducer using piezoelectric effects of a piezoelectric material. However, the transducer 105 is not limited thereto, and any transducer widely known in the art may be used.

The cMUT capable of being manufactured as ultrafine transducers using high integration technology is drawing more attention. Thus, the cMUT will be described in more detail with reference to FIGS. 8A and 8B.

Figure 8A:
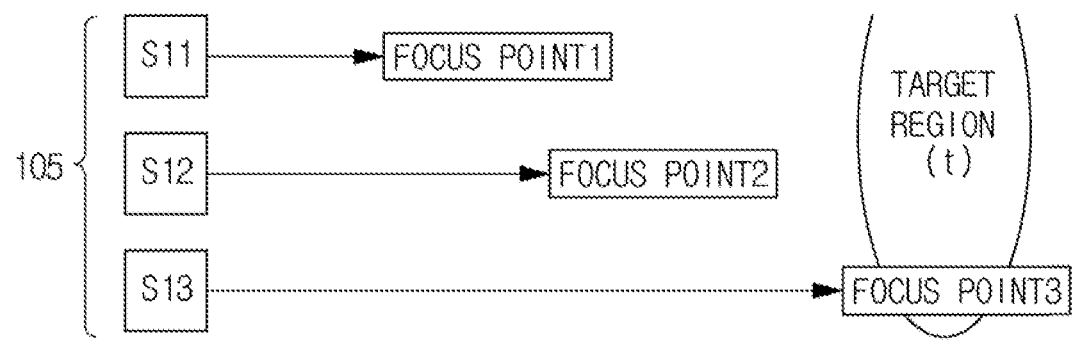
FIGS. 8A and 8B are diagrams for describing imaging by a capacitive micromachined ultrasonic transducer (cMUT)
Figure 8B:
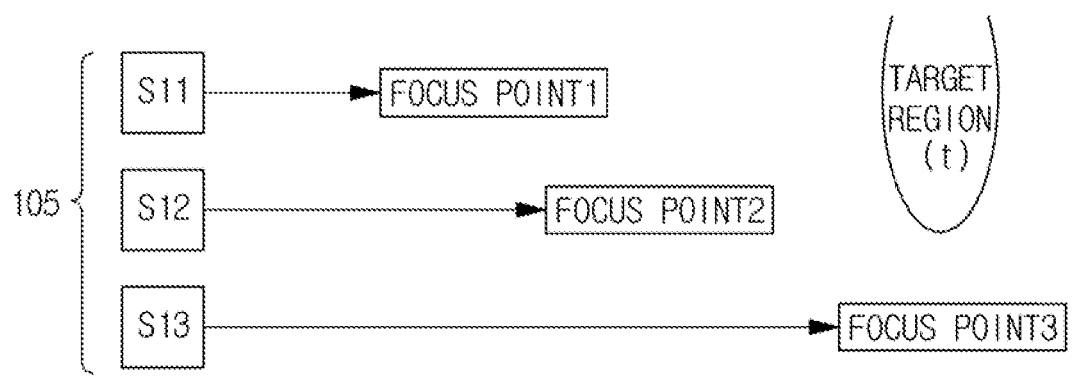

FIGS. 8A and 8B are diagrams for describing resolution by a capacitive micromachined ultrasonic transducer (cMUT).

A resultant image may include the target region of the object only when the target region of the object is located at the focus points of the element groups.

For example, under the condition that there are three element groups s11, s12, and s13 extending in the lateral direction A, and the first group s11 has a near field focus point (Focus Point 1), the second group s12 has a middle field focus point (Focus Point 2), and the third group s13 has a far field focus point (Focus Point 3) as illustrated in FIG. 8A, the target region may be displayed in an image at least when the target region is located at the far field focus point (Focus Point 3). Thus, when the target region is not located at the near field focus point or the middle field focus point, the size of the target region needs to be greater than the size of the three elements aligned in the azimuth direction Z.

In other words, when the target region of the object is neither located at the near field focus point nor at the middle field focus point, and the target region has a size corresponding to two elements in the azimuth direction Z, as illustrated in FIG. 8B, the target region cannot be displayed in the resultant image.

However, an element contained in the cMUT has a very small size, for example, a diameter of about 30 μm (a micrometer is $1 \times 10^{-6}$ meters) and a thickness of about 3,000 to 7,000 Å (an angstrom is $1 \times 10^{-8}$ meters). Thus, although an error by which the target region is not displayed in the resultant image occurs, the error may be negligible. Accordingly, a high resolution image may be acquired using the cMUT.

Figure 9:
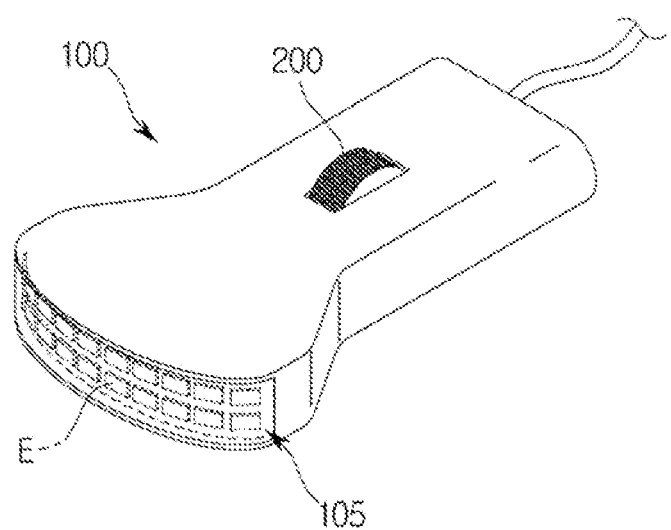
FIG. 9 is a perspective view illustrating a probe including a controller according to an exemplary embodiment.

FIG. 9 is a perspective view illustrating a probe including a frequency controller according to an exemplary embodiment.

The elements respectively transmit ultrasonic signals having a constant frequency toward the object and receive ultrasonic echo signals. In this case, propagation speed, degree of attenuation, and the like of ultrasonic signals may vary according to the type and structure of a medium of the object. Thus, the quality of the image may further be improved by adjusting the frequency of the ultrasonic signals transmitted by the elements to correspond to the medium of the object. In this regard, the medium of the object may be blood, fat, nerves, muscles, bones, and the like, but is not limited thereto.

For example, the aforementioned degree of attenuation of the ultrasonic waves varies according to properties of tissues, such as protein content and moisture content of tissues and increases in the order of blood, fat, nerves, muscle, skin, tendons, cartilage, and bone. Accordingly, the frequency of the ultrasonic waves may be controlled such that the frequency of the ultrasonic waves is decreased when the medium of the object is a bone having a high degree of attenuation, and the frequency may be increased when the medium of the object is blood having a low degree of attenuation.

The frequency may be controlled by increasing or decreasing all frequencies of ultrasonic signals transmitted toward the object by the element groups according to properties of the medium of the object. The transmit frequencies of the ultrasonic signals may be respectively controlled on a per group basis.

The position of a frequency controller 200 that controls a frequency band may vary. The frequency controller 200 may be disposed in the probe 100 as illustrated in FIG. 9 or may be disposed outside the probe 100, for example, in a controller 110 (FIG. 10).

The frequency controller 200 may be a scroll wheel as illustrated in FIG. 9 or a button according to a driving method thereof, but is not limited thereto.

The probe 100 of the ultrasonic imaging apparatus and functions of the probe 100 have been described. Hereinafter, the main body of the ultrasonic imaging apparatus will be described in more detail.

FIG. 10 is a block diagram illustrating an ultrasonic imaging apparatus according to an exemplary embodiment.

Referring to FIG. 10, the main body 300 may include a driver 120 that transmits a generated driving signal to the probe 100 and receives an echo signal from the probe 100, an image processor 130 that generates an image corresponding to the echo signal received from the driver 120, and a controller 110 that outputs a control command signal, stores data in a storage 112 (FIG. 11), or controls transmit frequency.

The driver 120 may include a transmit signal generator 121, a receive signal collector 122, and a beamformer 150.

The transmit signal generator 121 generates a driving signal to cause the probe 100 to transmit ultrasonic waves toward the object 96 in response to a command signal from the controller 110. The driving signal generated by the transmit signal generator 121 is transmitted to the probe 100.

The receive signal collector 122 receives the echo signal from the probe 100. In this regard, the echo signal refers to an electrically converted signal from the ultrasonic echo signal, which is received by the probe 100 from the object 96, by the transducer and has information regarding the target region t of the object 96. The receive signal collector 122 may also serve to output the received echo signals to the image processor 130.

The beamformer 150 may convert analog signals into digital signals, and vice versa. Thus, the beamformer 150 aids communication between the probe 100 and the driver 120 by converting the driving signal (digital signal) generated by the transmit signal generator 121 into an analog signal or by converting the echo signal (analog signal) received from the probe 100 into a digital signal.

The beamformer 150 may serve to apply a time delay to the digital signal in consideration of position and focus point of each of the elements in order to remove a time difference of arrival at the focus point between the ultrasonic waves or a time difference of arrival at each element from the focus point between the ultrasonic waves.

That is, a process of concentrating ultrasonic waves simultaneously emitted by a plurality of elements onto a focus point is referred to as focusing. The beamformer 150 may performs transmit focusing, by which ultrasonic waves respectively generated by the elements are sequentially emitted in a predetermined order to remove time difference of arrival at the focus point between the ultrasonic waves, and receive focusing, by which the ultrasonic echo signals are simultaneously aligned using predetermined time difference to remove time difference of arrival at each element between the ultrasonic echo signals.

The beamformer 150 may be disposed in the driver 150 as illustrated in FIG. 10 or outside the driver 150. That is, the beamformer 150 may be embodied in the main body 300 separately from the driver 120 or may be disposed in the probe 100 performing functions thereof.

The image processor 130 may include a signal processor 131 and an image obtainer 132.

The signal processor 131 may include an overall gain control process to amplify the overall size of the echo signal output from the driver 120. Since it is difficult to display the echo signal output from the driver 120 in a real image due to small size thereof, overall gain control is carried out before generation of the image. Here, the echo signal is a signal digitized by the beamformer 150.

Since the ultrasonic waves are attenuated while passing through the medium of the object 96, the signal processor 131 may perform time gain compensation (TCG) to compensate for such attenuation and amplify the echo signal in proportion to the distance from the target region.

The signal processor 131 may conduct filtering, i.e., remove low level noises from the echo signal, to obtain a clear signal.

The image obtainer 132 acquires an image corresponding to the echo signal output from the driver 120, particularly, an image corresponding to a signal subjected to a variety of processes by the signal processor 131.

The acquired image may include at least one image selected from the group consisting of images acquired according to different focal distances of the element groups and a multi-focus ultrasonic image acquired by combing the images. The multi-focus ultrasonic image refers to an ultrasonic image obtained by combining a plurality of images acquired according to a plurality of focal distances when the ultrasonic imaging apparatus has a plurality of focus points or focal distances due to non-uniform distance or depth between a reference plane, which is a contact plane of the probe 100 in this case, and a target region, which is a region to be diagnosed.

The combined multi-focus ultrasonic image may be acquired by simply overlapping all of the images or by selecting partial images corresponding to the near sound filed based on the focal distance and overlapping the partial images, but is not limited thereto.

The acquired image may be a black-and-white image having only brightness corresponding to each pixel, which is represented by x and y coordinates when the image is a two-dimensional image, or a color image having brightness, saturation, and hue corresponding to each pixel.

The image obtainer 132 may further perform compression for storing image data and may transmit the image data to the display 140 so as to display the generated image on the screen.

Figure 11:
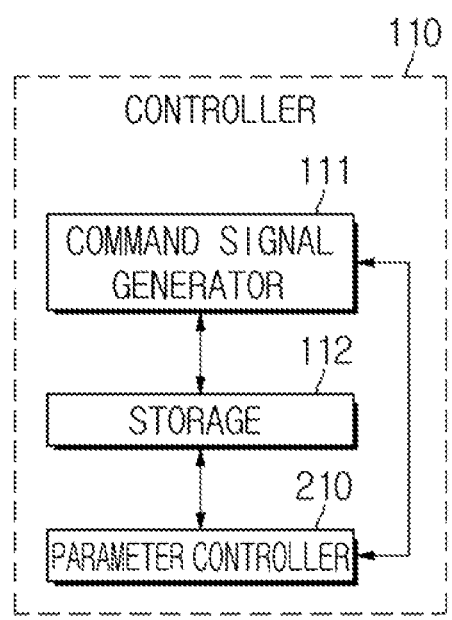
FIG. 11 is a block diagram illustrating a controller of an ultrasonic imaging apparatus according to an exemplary embodiment.

FIG. 11 is a block diagram illustrating a controller of an ultrasonic imaging apparatus according to an exemplary embodiment.

The controller 110 may include a command signal generator 111, a storage 112, and a parameter controller 210.

The command signal generator 111 may output a control command signal to the driver 120.

When a user inputs a command to perform ultrasonic imaging to an input unit 400, the command signal generator 111 outputs a command signal to transmit ultrasonic waves toward the object 96 to the driver 120.

The command signal generator 111 may simultaneously output a command signal regarding the frequency band of the ultrasonic waves to be transmitted to the driver 120. In this regard, the command signal may include a frequency input by the user according to the medium of the object 96 or may include a frequency preset according to the medium of the object and auto-selected.

The command signal generator 111 may output the control command signal to the image processor 130.

The command signal generator 111 may output a command signal to display the generated image on the display 140 to the image processor 130. The command signal may be output such that all of the images acquired according to different focus points of the element groups and the multi-focus ultrasonic image acquired by combination of the images are displayed, or such that only the multi-focus ultrasonic image is displayed. This process may be selected by the user through the input unit 400 or may be conducted according to a preset method.

The command signal generator 111 may simultaneously output a command signal regarding a screen display mode to the image processor 130. The screen display mode may include an A-mode to display the intensity of the echo signal as amplitude, a B-mode using brightness or luminance, an M-mode to display a distance from a moving target region using variation of time, a D-mode using a pulse wave or continuous wave, and a color flow mapping (CFM)-mode to display a color image using the Doppler effect, but is not limited thereto. The command signal may be output using an automatically selected display mode according to the position, size, and shape of the target region or a display mode input according to the user's determination.

The storage 112 may store data or algorithms for manipulation of the ultrasonic imaging apparatus. For example, the storage 112 may store various parameters such as transmit frequency according to the distance from the target region t or the medium of the object 96, compressed data of images generated by the image processor 130, pixel of the image and brightness of each pixel, screen display mode according to the properties of the target region t, and the like. The storage 112 may also store algorithms to generate the image, algorithms to combine the images acquired according to the focal distance, and the like.

The storage 112 may be implemented as a storage device, for example, a nonvolatile memory device such as a read only memory (ROM), a programmable read only memory (PROM), an erasable programmable read only memory (EPROM), and a flash memory, a volatile memory such as a random access memory (RAM), a hard disk, and an optical disc. However, the storage 112 is not limited thereto, and any other storage units known to those skilled in the art may also be used.

The parameter controller 210 is connected between the input unit 400 and the command signal generator 111, thereby controlling various parameters for driving the ultrasonic imaging apparatus, performing screen output, and the like.

As an example of controlling parameters, frequency of the ultrasonic signal may be controlled according to the medium of the object 96. That is, when the input unit 400 receives information regarding the medium of the object 96, the parameter controller 210 examines properties of the medium, automatically selects a frequency band of the ultrasonic signal preset according to properties of the medium, and transmits the selected frequency band to the command signal generator 111. The necessity of adjustment of the transmit frequency has been described above, and thus a detailed description thereof will not be given here.

For example, all frequencies of the ultrasonic signals transmitted from the element groups toward the object 96 may be controlled to be increased or decreased according to the medium. Alternatively, frequencies may be selected in groups in accordance with the element groups having different focal distances.

As another example of controlling parameters, upon receiving the brightness (luminance) level, size, direction, or the like of an image to be displayed on the screen from the input unit 400, the parameter controller 210 may modify image data according thereto and transmit the data to the command signal generator 111. As a result, the user may efficiently observe the target region t of the object 96 and obtain required information.

Figure 12:
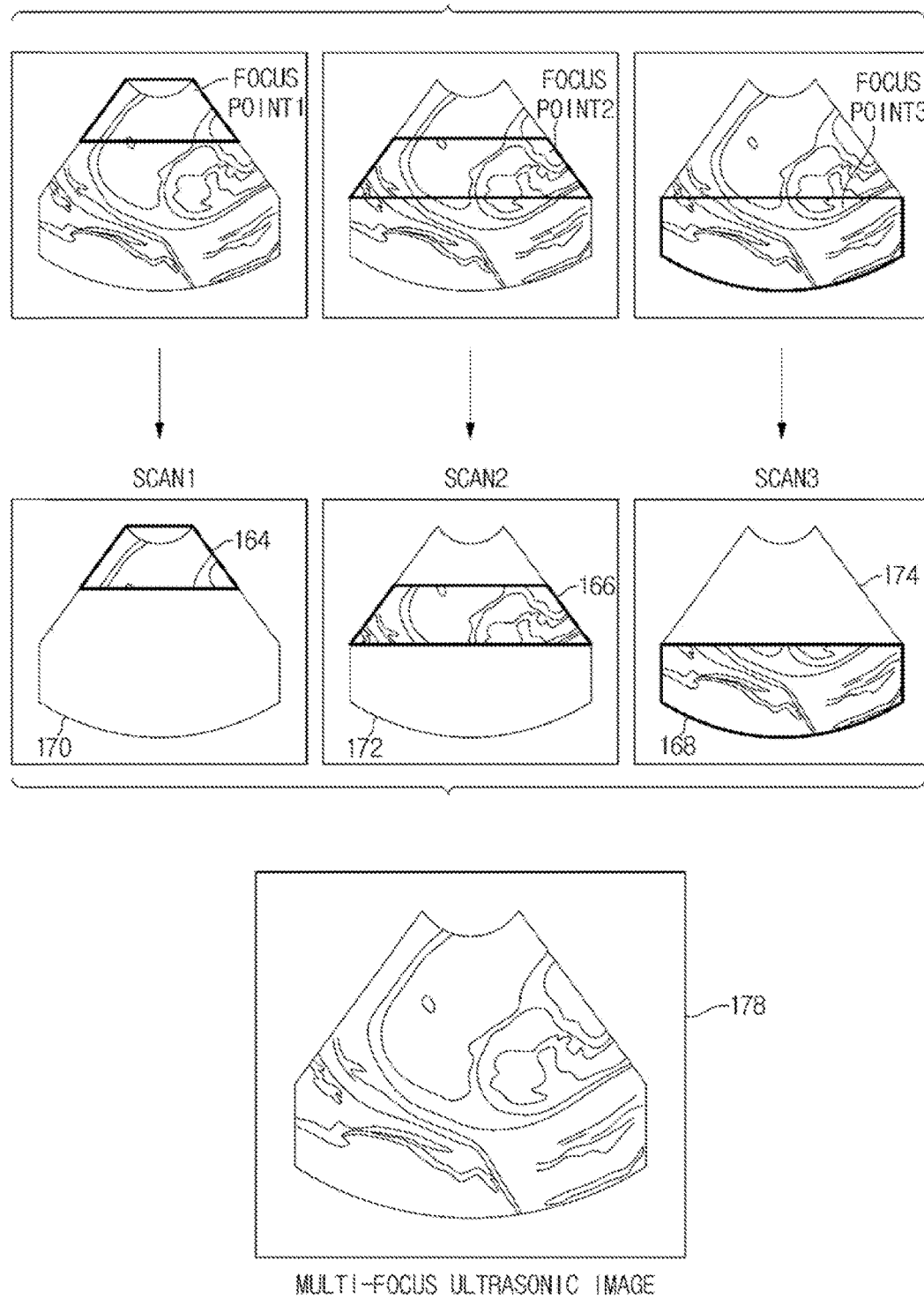
FIG. 12 illustrates images acquired by an ultrasonic imaging apparatus according to focal distance and a multi-focus ultrasonic image.

FIG. 12 illustrates images acquired by an ultrasonic imaging apparatus according to focal distance and a multi-focus ultrasonic image.

As illustrated in FIG. 12, when the element groups s11, s12, and s13 having different focus points Focus Point 1, Focus Point 2, and Focus Point 3, which is described above, simultaneously transmit ultrasonic waves toward the object 96, images corresponding thereto are respectively output as Scan 1, Scan 2, and Scan 3 as illustrated in FIG. 12.

As described above with regard to the near field as a factor of setting the focus point, a portion of each of the ultrasonic images within a reference focal area of each element group has high resolution (reference numerals 164, 166, 168), but portions not within the focal area (reference numerals 170, 172, 174) have deteriorated resolution. Thus, quality of the portions of the images not within the focal area is deteriorated in each scan image.

Thus, a multi-focus ultrasonic image 178 having improved quality in all areas is generated by combining three images output in accordance with different focal distances Scan 1, Scan 2, and Scan 3.

In this case, when the element groups are s11, s12, and s13 as illustrated in FIG. 7, the element groups may transmit ultrasonic signals having different frequencies, i.e., ultrasonic signals with a high frequency (Focus Point 1), ultrasonic signals with a middle frequency (Focus Point 2), and ultrasonic signals with a low frequency (Focus Point 3), according to the focal distance toward the object. As a result, a higher-quality multi-focus ultrasonic image may be acquired.

Constituent elements of the ultrasonic imaging apparatus and functions thereof have been described based on exemplary embodiments. Hereinafter, a method of controlling an ultrasonic imaging apparatus will be described with reference to FIG. 13.

FIG. 13 is a flowchart illustrating a method of controlling an ultrasonic imaging apparatus according to an exemplary embodiment.

Referring to FIG. 13, frequency bands of ultrasonic signals transmitted from the element groups toward the object are automatically or manually controlled (operation S300).

This operation, as a process for acquiring a high-quality image, is carried out before the element groups transmit ultrasonic signals toward the object, since propagation speed, degree of attenuation, and the like, of ultrasonic waves vary according to the medium of the object. This operation may also be conducted after output of a signal (operation S310), i.e., between operation S310 and operation S320.

This operation may be performed by controlling all frequencies of the ultrasonic signals transmitted from the element groups toward the object according to the medium of the object or by controlling transmit frequencies of the ultrasonic signals in groups according to the element groups.

The user may directly input frequency to be transmitted according to the medium of the object. Alternatively, the user may input only information regarding the medium, and then frequency band may be automatically selected based thereon among the preset frequencies.

Then, the controller 110 outputs a control command signal to transmit ultrasonic signals toward the object (operation S310).

When the control command signal is output, the driver 120 outputs a driving signal to cause the probe 100 to transmit ultrasonic waves toward the object. Since the driving signal is output after receiving the command signal, the driving signal plays a direct role in the transmission of ultrasonic waves.

In response to the driving signal, the element groups transmit ultrasonic signals toward the object (operation S320).

In this operation, the element groups respectively having different focal distances simultaneously transmit the ultrasonic signals toward the object, i.e., the element groups, each including a plurality of elements with the same focal distance, may transmit the ultrasonic signals.

The element groups having different focal distances may simultaneously transmit ultrasonic signals having different frequencies according to focal distance toward the object. The transmit frequency may be inversely proportional to the corresponding focal distance.

Then, the element groups receive echo signals from the object in accordance with each focal distance (operation S330).

Here, when the element groups transmit ultrasonic signals having different frequencies toward the object according to the focal distance, the echo signals received from the object may be classified into groups in accordance with the frequencies.

For example, when the element groups s11, s12, and s13 transmit ultrasonic signals having different frequencies, such that the first group s11 transmits ultrasonic signal having a first frequency f1, the second group s12 transmits ultrasonic signal having a second frequency f2, and the third group transmits ultrasonic signal having a third frequency f3, the first group s11 receives ultrasonic echo signals having the first frequency f1, the second group s12 receives ultrasonic echo signals having the second frequency f2, and the third group s13 receives ultrasonic echo signals having the third frequency f3.

Then, an ultrasonic image is generated according to the echo signal (operation S340), and this process has the following sub-operations.

The probe 100 outputs an electrical signal converted from the received echo signal (ultrasonic echo signal) by the transducer 105. The output echo signals are digitized and collected by the beamformer 150 and transmitted to the image processor 130 to generate an image.

Images are generated from the received echo signals according to the focal distance of the element groups. By further performing a combination of the generated images, a multi-focus ultrasonic image may be generated.

During this process, the storage 112 may store image data, and the method may further include a process of compressing the image data.

After the ultrasonic image is generated (operation S340), the controller 110 transmits a control command signal to display an image (operation S350).

As an example of an image display command, a command signal to display the generated image on a screen may be output.

The user may select whether to display the image on the screen, or the command signal may be output such that the image may be automatically displayed on the screen regardless of the user's selection. In case of the user's selection, when the user does not agree to display the image on the screen ②, the process is ended immediately after generating the image, differently from the case in which the user agrees to display the image on the screen ①.

As another example of the image display command, a command signal to display all images acquired according to different focal distances of the element groups and the multi-focus ultrasonic image acquired by combination of the images, or to display only the multi-focus ultrasonic image on the screen, may be output.

The user may select the image to be displayed on the screen. Alternatively, a command signal may be output such that only the multi-focus ultrasonic image may be automatically displayed on the screen regardless of the user's selection.

As another example of the image display command, a command signal regarding the screen display mode such as the commonly used A-mode, B-mode, M-mode used to record status of the artery during heart valve or abdominal scanning and fetal heart rate, and D-mode and CFM-mode used to diagnose reverse blood flow, stricture at the heart valve, congenital heart disease, and the like, by measuring speed and direction of blood stream, may be output.

The screen display mode may be selected by the user, or a command signal may be output such that the image may be automatically displayed in a preset mode according to the property of the target region regardless of the user's selection.

The image is displayed on the screen according to the predetermined screen display mode upon the user's approval ① or the command to automatically display the image (operation S360).

As is apparent from the above description, according to the ultrasonic imaging apparatus and the method of controlling the same, the multi-focus ultrasonic image may be quickly acquired so as to increase frame rates.

Furthermore, a high-quality image having all areas focused may be acquired at high speed.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An ultrasonic imaging apparatus comprising:
   an ultrasonic probe comprising a multi-dimensionally arrayed transducer comprising elements which are arranged in element groups having focal distances different from one another in correspondence with different frequencies, with respect to an object, the focal distances being determined by a frequency which has been set for each of the element groups, respectively, and are configured to simultaneously transmit ultrasonic signals toward the object and receive echo signals reflected from the object;
   a controller configured to set the frequency of the ultrasonic signals variously for each of the element groups and output a control command signal to cause the ultrasonic probe to transmit the ultrasonic signals; and
   an image processor configured to generate a first image based on the echo signals received in response to transmitting the ultrasonic signals according to a first focal distance, of the focal distances, generate a second image based on the echo signals received in response to transmitting the ultrasonic signals according to a second focal distance, of the focal distances, and generate a multi-focal image by combining the first image and the second image that are generated according to the first focal distance and the second focal distance, respectively,
   wherein the controller is further configured to additionally adjust the set frequency of the ultrasonic signals of the element groups based on a characteristic of the object,
   the different frequencies include a first frequency, a second frequency, and a third frequency,
   the element groups simultaneously transmit the ultrasonic signals having the first frequency according to the first focal distance, the second frequency according to the second focal distance, and the third frequency according to a third focal distance, of the focal distances, and the first frequency, the second frequency, and the third frequency respectively decrease as the first focal distance, the second focal distance, and the third focal distance respectively increase.

2. The ultrasonic imaging apparatus according to claim 1, wherein each of the element groups comprises the elements having a same focal distance within a corresponding element group.

3. The ultrasonic imaging apparatus according to claim 1, wherein the elements of the multi-dimensionally arrayed transducer are two-dimensionally arrayed in a matrix having rows in a lateral direction and columns in an azimuth direction, and the element groups comprise m groups in which the elements are grouped by the rows extending in the lateral direction, or n groups in which the elements are grouped by the columns extending in the azimuth direction, and m is a natural number of 2 or more and n is a natural number of 2 or more.

4. The ultrasonic imaging apparatus according to claim 1, further comprising a display to display the multi-focal image.

5. The ultrasonic imaging apparatus according to claim 1, wherein the controller is further configured to output a control command signal to display the multi-focal image.

6. The ultrasonic imaging apparatus according to claim 1, wherein the first focal distance corresponds to a near field focus point and the first frequency corresponds to a highest frequency, the second focal distance corresponds to a far field focus point and the second frequency corresponds to a lowest frequency, and the third focal distance corresponds to a middle field focus point and the third frequency is between the highest frequency and the lowest frequency, of the different frequencies.

7. The ultrasonic imaging apparatus according to claim 1, further comprising:

a display configured to display together the multi-focal image and at least one from among the first image and the second image, on a screen of the display.

8. The ultrasonic imaging apparatus according to claim 1, wherein the elements of the multi-dimensionally arrayed transducer are arranged in a rectangular matrix having at least two rows each having an equal number of the elements in a lateral direction and at least two columns each having an equal number of the elements in an azimuth direction, and the image processor is further configured to generate the first image at the first focal distance based on the echo signals received in response to the ultrasonic signals transmitted by all of the elements arranged in a first row of the at least two rows, and to generate the second image at the second focal distance based on the echo signals received in response to the ultrasonic signals transmitted by all of the elements arranged in a second row of the at least two rows, the first row being disposed adjacent the second row.

9. The ultrasonic imaging apparatus according to claim 1, further comprising:

a frequency controller coupled to the controller and configured to receive a selection input of a user for adjusting the frequency of the ultrasonic signals based on the characteristic of the object.

10. The ultrasonic imaging apparatus according to claim 9, wherein the frequency controller is further configured to increase or decrease all of the different frequencies of the ultrasonic signals transmitted toward the object by the element groups, based on the selection input and the characteristic of the object.

11. The ultrasonic imaging apparatus according to claim 9, wherein the frequency controller comprises a button or a scroll wheel.

12. A method of controlling an ultrasonic imaging apparatus, the method comprising:

simultaneously transmitting via an ultrasonic probe comprising a multi-dimensionally arrayed transducer comprising elements arranged in element groups, ultrasonic signals toward an object by the element groups having focal distances different from one another in correspondence with different frequencies, with respect to the object, the focal distances being determined by a frequency which has been set for each of the element groups, respectively;

receiving echo signals from the object by the element groups;

providing a controller that is programmed to set the frequency of the ultrasonic signals variously for each of the element groups and output a control command signal to cause the ultrasonic probe to transmit the ultrasonic signals; and via an image processor, generating a first image based on the echo signals received in response to the ultrasonic signals transmitted according to a first focal distance, of the focal distances;

generating a second image based on the echo signals received in response to the ultrasonic signals transmitted according to a second focal distance, of the focal distances; and generating a multi-focal image by combining the first image and the second image that are generated according to the first focal distance and the second focal distance, respectively, wherein the simultaneously transmitting comprises transmitting, by the element groups, the ultrasonic signals of which the set frequency is additionally adjusted based on a characteristic of the object, the different frequencies include a first frequency, a second frequency, and a third frequency, the simultaneously transmitting further comprises simultaneously transmitting, via the element groups, the ultrasonic signals having the first frequency according to the first focal distance, the second frequency according to the second focal distance, and the third frequency according to a third focal distance, of the focal distances, and the first frequency, the second frequency, and the third frequency respectively decrease as the first focal distance, the second focal distance, and the third focal distance are respectively increase.

13. The method according to claim 12, wherein each of the element groups comprises the elements having a same focal distance within a corresponding element group.

14. The method according to claim 12, further comprising displaying the multi-focal image.

15. The method according to claim 12, further comprising outputting a control command signal to display the multi-focal image.

* * * * *